(12) United States Patent
Shichman et al.

(10) Patent No.: US 6,197,041 B1
(45) Date of Patent: Mar. 6, 2001

(54) TROCAR

(75) Inventors: Daniel Shichman; David A. Nicholas, both of Trumbull; Ernie Aranyi, Easton, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 08/122,612

(22) Filed: Sep. 15, 1993

Related U.S. Application Data

(63) Continuation of application No. 07/721,173, filed on Jun. 26, 1991.

(51) Int. Cl.[7] .................................................. A61B 17/34

(52) U.S. Cl. ...................................... 606/185; 604/164.12

(58) Field of Search ............................ 606/185; 604/164, 604/167, 156, 164.01, 164.12

(56) References Cited

U.S. PATENT DOCUMENTS

| | | |
|---|---|---|
| 1,147,408 | 7/1915 | Kells . |
| 1,213,001 | 1/1917 | Philips . |
| 2,097,039 | 10/1937 | Peterson . |
| 2,525,329 | 10/1950 | Wyzenbeek . |
| 3,030,959 | 4/1962 | Grünert . |
| 3,561,429 | 2/1971 | Jewett . |
| 3,643,649 | 2/1972 | Amato . |
| 3,727,613 | 4/1973 | Sorenson et al. . |
| 3,752,161 * | 8/1973 | Bent ..................................... 606/184 |
| 3,762,416 | 10/1973 | Moss et al. . |
| 3,789,752 | 2/1974 | Kim et al. . |
| 3,882,849 | 5/1975 | Jamshidi . |
| 3,948,271 | 4/1976 | Akiyama . |
| 3,994,287 | 11/1976 | Turp et al. . |
| 4,013,080 | 3/1977 | Froning . |
| 4,177,814 | 12/1979 | Knepshield et al. . |
| 4,191,191 | 3/1980 | Auburn . |
| 4,230,123 | 10/1980 | Hawkins, Jr. . |
| 4,254,762 | 3/1981 | Yoon . |
| 4,299,230 | 11/1981 | Kubota . |
| 4,356,826 | 11/1982 | Kubota . |
| 4,375,815 | 3/1983 | Burns . |
| 4,393,587 | 7/1983 | Kloosterman . |
| 4,411,653 | 10/1983 | Razi . |
| 4,413,985 | 11/1983 | Wellner et al. . |
| 4,535,373 | 8/1985 | Yoon . |
| 4,556,059 | 12/1985 | Adamson, Jr. . |
| 4,559,041 | 12/1985 | Razi . |
| 4,601,710 | 7/1986 | Moll . |
| 4,654,030 | 3/1987 | Moll et al. . |
| 4,696,298 | 9/1987 | Higgins et al. . |
| 4,713,057 | 12/1987 | Huttner et al. . |

(List continued on next page.)

FOREIGN PATENT DOCUMENTS

| | | |
|---|---|---|
| 938979 | 2/1956 | (DE) . |
| 350291A3 | 10/1990 | (EP) . |
| 0479130 | 4/1992 | (EP) . |
| 0495633 | 7/1992 | (EP) . |
| 0499457 | 8/1992 | (EP) . |
| 0630619 | 12/1994 | (EP) . |
| WO 86 00815 | 2/1986 | (WO) . |

*Primary Examiner*—Michael H. Thaler

(57) ABSTRACT

A pneumatically powered trocar assembly includes a source of compressed gas which releases a metered amount of gas to a chamber. A piston slidably positioned within the chamber is driven forward by the compressed gas introduced therein, and an obturator with a tissue piercing tip are advanced thereby. Optionally, a sensor detects the presence of body tissue within the cutting path of the tip and blocks the passage of compressed gas to the chamber, or alternatively, opens an escape vent to release compressed gas therefrom if insufficient body tissue resistance is encountered. The powered trocar assembly is intended for use in conjunction with a cannula assembly to create a passage to the interior of a body cavity for conducting surgical procedures.

21 Claims, 13 Drawing Sheets

U.S. PATENT DOCUMENTS

| | | |
|---|---|---|
| 4,723,545 | 2/1988 | Nixon et al. . |
| 4,733,662 | 3/1988 | DeSatnick et al. . |
| 4,733,671 | 3/1988 | Mehl . |
| 4,747,831 | 5/1988 | Kulli . |
| 4,931,042 | 6/1990 | Holmes et al. . |
| 5,104,382 | 4/1992 | Brinkerhoff et al. . |
| 5,152,754 * | 10/1992 | Plyley et al. ............ 604/164 |
| 5,188,118 | 2/1993 | Terwilliger . |

\* cited by examiner

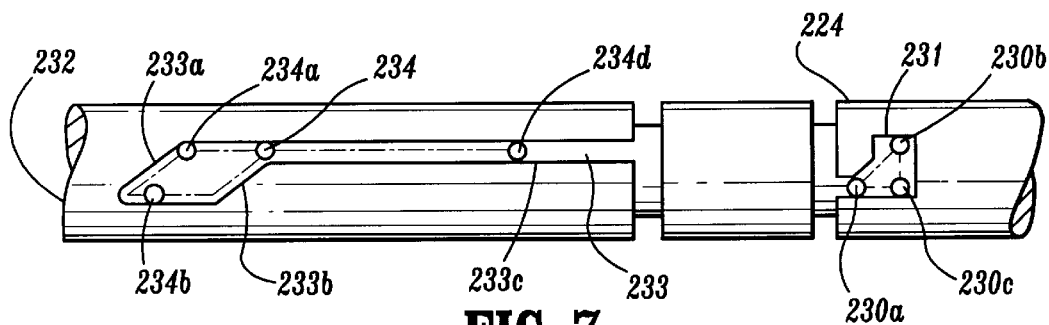
FIG. 7
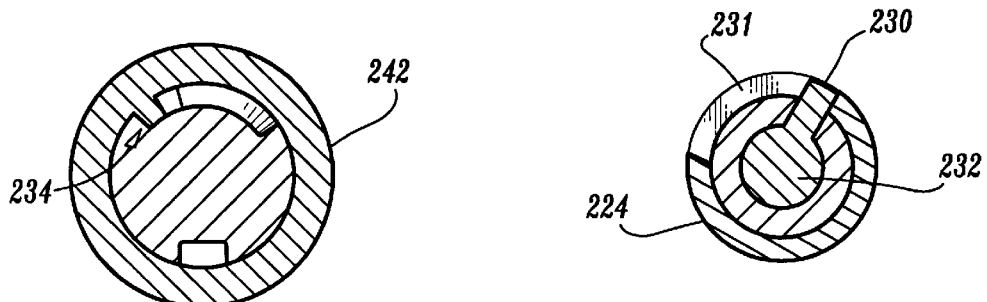
FIG. 8
FIG. 9
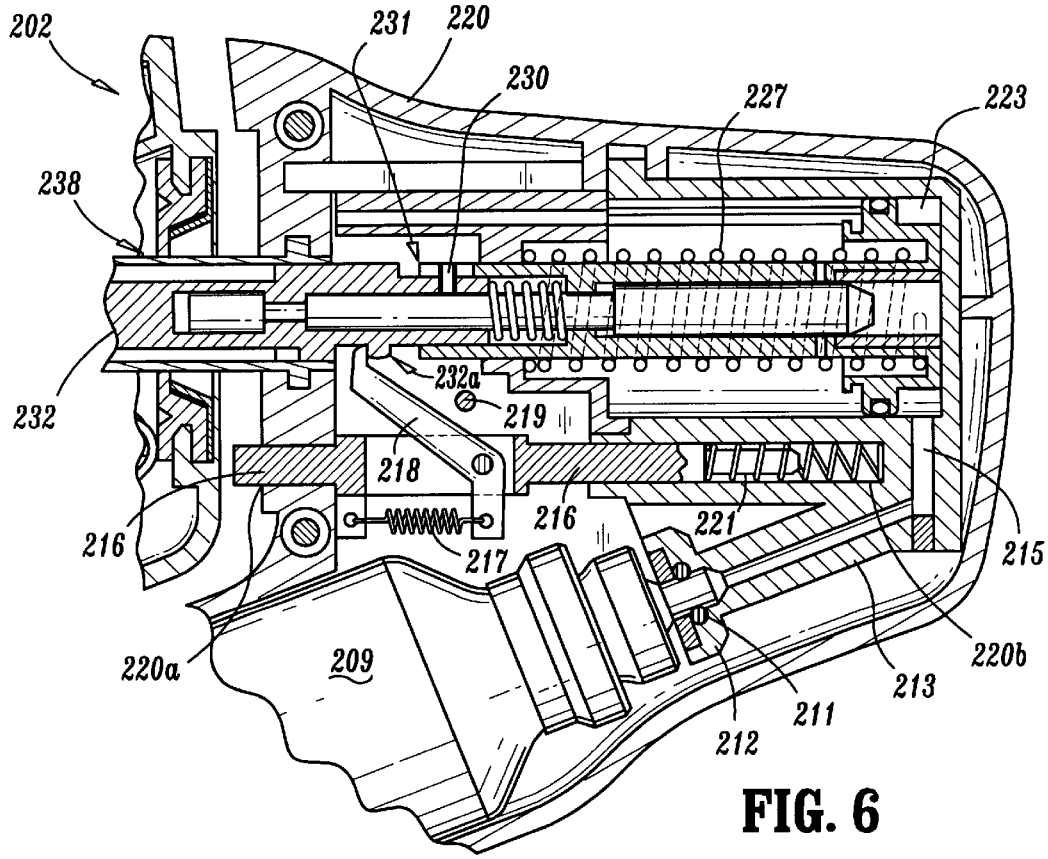
FIG. 6

TROCAR

This is a continuation, of copending application Ser. No. 07/721,173 filed on Jun. 26, 1991.

BACKGROUND OF THE INVENTION

1. Field of the Invention

This invention relates to a surgical instrument for piercing or puncturing a wall of body tissue to provide communication with the inside of an anatomical cavity, and more particularly this invention relates to a powered trocar with an optional safety feature for preventing the unintended puncturing of body tissue.

2. Background of the Art

Many medical procedures gain access to the inside of an anatomical cavity by using an implement such as a trocar, cannula or needle having a sharpened point to pierce or puncture the bodily tissues, muscles and membranes forming the cavity wall. A surgical needle, for example, connected to a catheter may be used to pierce a cavity (blood vessel, subarachnoid space, heart ventricle). After piercing the cavity, the needle is left in situ and used to inject or withdraw gaseous or liquid phase fluids from the cavity. similarly, in several endoscopic procedures, a small incision may be made in the skin of a patient along the abdomen for example, and the sharp point of a larger penetrating implement such as a trocar of suitable length and diameter is inserted into the incision, and pushed until the point punctures the cavity wall. Then, a sleeve follows the implement into the puncture wound to preserve the shape of the passageway created by the implement. After the sleeve is in place, the implement may be withdrawn and an endoscope and operating instruments may be inserted via the sleeve to view and operate upon organs within the cavity. Endoscopic instruments are those instruments having a relatively narrow and elongated portion for use in endoscopic surgical procedures wherein such instruments create or are inserted through a small diameter puncture in order to carry out surgical procedures within a human or animal body.

Penetrating the wall of an anatomical cavity with a surgical puncturing instrument can be quickly done and, usually creates a small neat passageway providing communication to the interior of the cavity. While the sharp point of a penetrating implement is being pushed through a cavity wall, it encounters great resistance from the tissue, muscle and membranes forming the cavity wall. Once the sharp point and blade of the implement pass through the cavity wall and into the cavity, the resistance drops significantly. The sharp point of the implement, however, can easily injure organ structure within the cavity upon the slightest contact. Unless a surgeon stops pushing the implement just as soon as penetration is complete, there is a risk that the implement will continue penetrating deeply into the cavity and injure neighboring organ structure. If an unintended bodily member is injured by the point of the implement, there is a risk that the injury may not become apparent until after completion of the surgery. At a minimum, such an injury will delay a patient's recovery. Severe injuries of this type may endanger the patient's health, and corrective surgery may be required.

Various instruments have been developed to deal with this problem. For example, U.S. Pat. No. 4,601,710 discloses a surgical instrument having a spring biased movable shield which retracts into a cannula to expose the sharp trocar tip when pressed against body tissue, but which moves forward to protect body tissue from contact with the trocar tip when the instrument has passed through the wall of body tissue.

While the instrument described in U.S. Pat. No. 4,601,710 provides an added degree of safety as opposed to an instrument without a shield, the aforementioned problem remains: the sudden drop in the resistance to the trocar blade when penetration has been made into the body cavity increases the chance of uncontrolled continued penetration and possible damage to the underlying body tissue. Moreover, tissue trauma may result from the shield. To alleviate this problem a powered trocar has been developed.

SUMMARY OF THE INVENTION

Presented herein is a pneumatically powered trocar assembly which includes a source of compressed gas which releases a metered amount of gas to chamber. A piston slidably positioned within the chamber is driven forward by the compressed gas introduced therein, and an obturator with a tissue piercing tip are advanced thereby. Optionally, a sensor detects the presence of body tissue within the cutting path of the tip and blocks the passage of compressed gas to the chamber, or alternatively, opens an escape vent to release compressed gas therefrom if insufficient body tissue resistance is encountered.

More particularly, the powered trocar assembly of the present invention includes a frame, a tissue piercing tip, drive means housed by the frame for advancing the tissue piercing tip in response to the application of pneumatic power, trigger means for releasing a predetermined quantity of compressed gas from a source thereof, and means for communicating said quantity of compressed gas to a chamber. The drive means includes a piston movable within said chamber in response to the entry or egress of compressed gas therein, and an obturator shaft mounted to said piston, the tissue piercing tip being mounted to the distal end of said obturator shaft.

The obturator may alternatively be fixedly mounted to the piston, or slidably mounted thereto. The apparatus may optionally include sensing means projecting distally beyond the cutting tip and movable proximally against a distal biasing force to indicate the presence of body tissue in the cutting path of the trocar tip. In another alternative the cutting tip serves as the sensing means by causing the release of compressed gas from the chamber if insufficient tissue resistance is encountered.

Activation of the apparatus, which places it in a ready to fire condition, may be accomplished by actuation of the tissue sensing means, or by assembling and firmly holding together the powered trocar with a cannula assembly.

BRIEF DESCRIPTION OF THE DRAWINGS

FIG. 6 is a partially cut-away sectional view of the proximal end of the second embodiment of the apparatus in prefired and preactivated condition.

FIG. 7 illustrates a side view of the drive mechanism of the present invention;

FIGS. 8 and 9 illustrate sectional view of the drive mechanism of the present invention.

DETAILED DESCRIPTION OF PREFERRED EMBODIMENTS

The powered trocar assembly of the present invention is a pneumatically driven trocar assembly for penetrating body tissue. The powered trocar assembly optionally can be configured into different conditions. In the description below, the activated condition refers to the condition wherein the powered trocar can be fired by depressing the trigger. In the fired condition the cutting tip advances distally beyond the cannula so as to penetrate body tissue. The powered trocar of the present invention is preferably configured so that it cannot be fired unless it is in the activated condition.

Generally, the trocar assembly of the present invention includes a distal cannula portion and the powered trocar. The powered trocar and the cannula portion are assembled by inserting the endoscopic portion of the powered trocar including cutting tip, elongated obturator, and actuator (if applicable) through the cannula. The powered trocar assembly is then used as described more fully below to create an incision in the body tissue. When the incision is completed and a passageway is created to the interior of the body cavity, the powered trocar may be removed from the assembly, leaving the cannula inserted in the body. A surgical operation may then be performed in the body cavity by inserting other endoscopic instruments through the cannula. More than one cannula may be deployed so as to create separate channels for fiber optic viewing and lighting, insufflation/desufflation, cutting and cauterizing, and so forth. A pivotally mounted flapper is spring-biased to close the aperture when the endoscopic instruments are removed from the cannula portion, thereby preventing the escape of gas from the insufflated body cavity. When the operation has been completed, the cannula portion is removed.

FIRST EMBODIMENT

Figures 1, 2A:
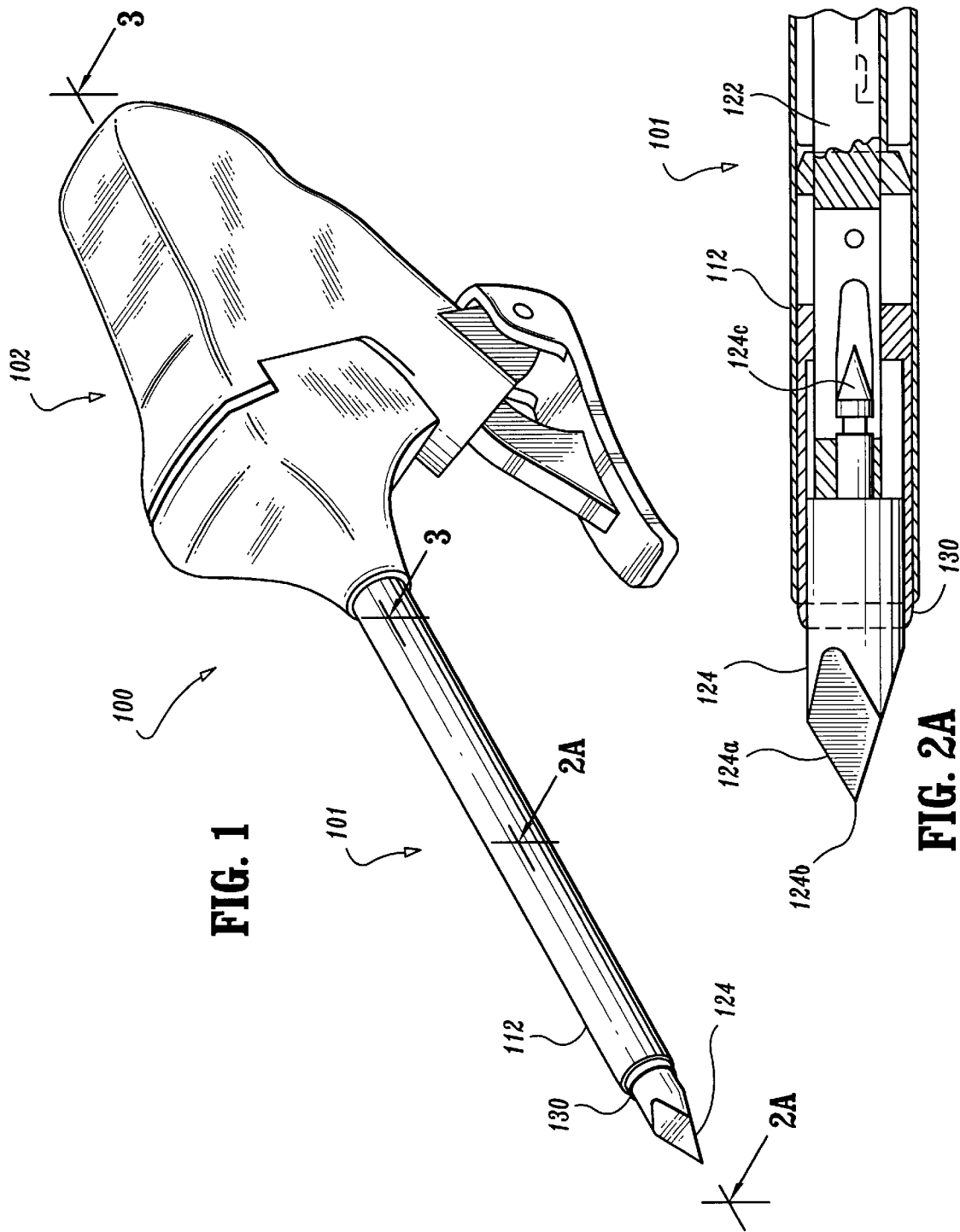
FIG. 1 is a perspective view of the apparatus of the present invention.
FIGS. 2a and 2b are sectional views of the distal end of the apparatus of the present invention.
Figure 2B:
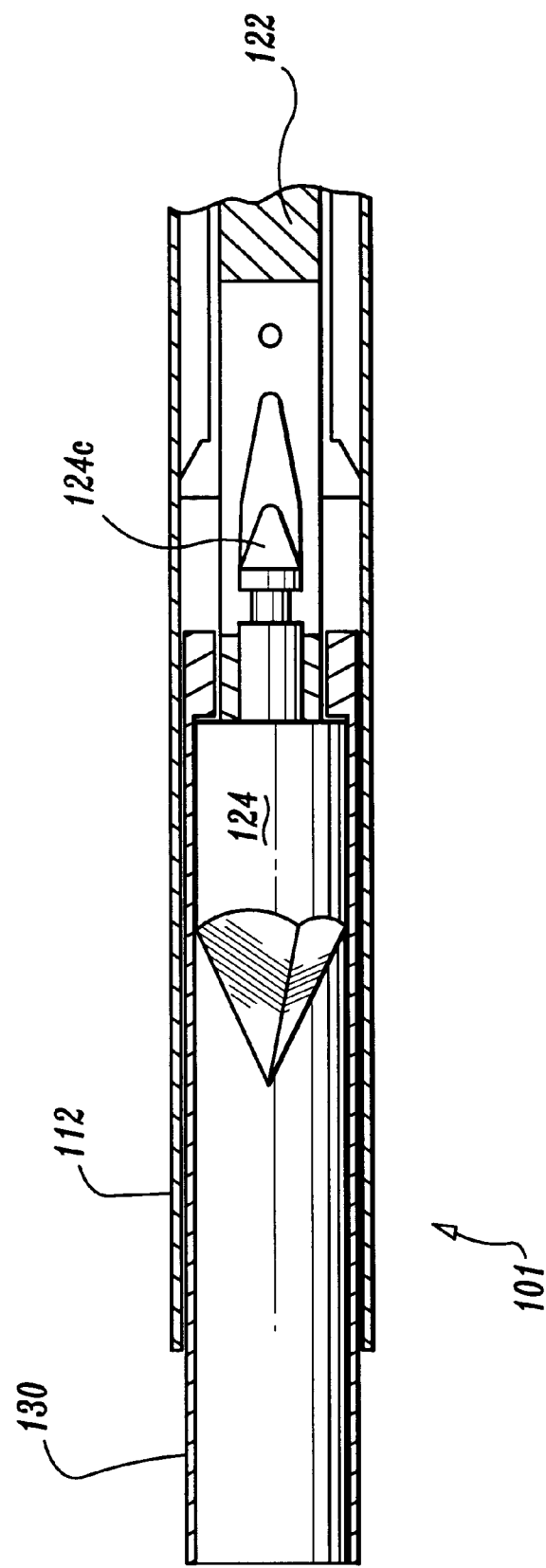

Referring to FIGS. 1, 2a and 2b, powered trocar assembly 100 of the present invention includes a valve assembly 101 having a housing 114 and a cannula portion 112 for insertion through body tissue, and a powered trocar 102 for puncturing and penetrating body tissue. The powered trocar 102 also includes an actuator tube 130 which provides means for putting the powered trocar 102 in an activated (i.e., ready to fire) condition.

Referring more particularly to FIGS. 2a and 2b, the cutting tip 124 has sharp edges 124a which terminate in a sharp point 124b for penetration of body tissue. The proximal end of tip 124 includes a fixture 124c for mounting to the distal end of obturator shaft 122. Actuator tube 130 surrounds shaft 122 and tip 124. Both the actuator tube 130 and shaft 122 are slidably movable within cannula 112. In the initial unfired and inactivated condition of the instrument as shown in FIG. 2b, actuator tube 130 extends outwardly beyond the distal end of cannula 112. The trocar tip is initially inside cannula 112, which functions to shield the tip. When the instrument is pressed against body tissue the actuator 130, which is resiliently biased towards the distal position, is made to retract proximally into cannula 112 thereby activating the powered trocar assembly. When the instrument is fired the trocar tip 124 is advanced out beyond the distal end of cannula 112 to a predetermined distance as shown in FIG. 2a so as to pierce the body tissue. Further details about the operation of the powered trocar assembly 100 will be given below.

Figure 3:
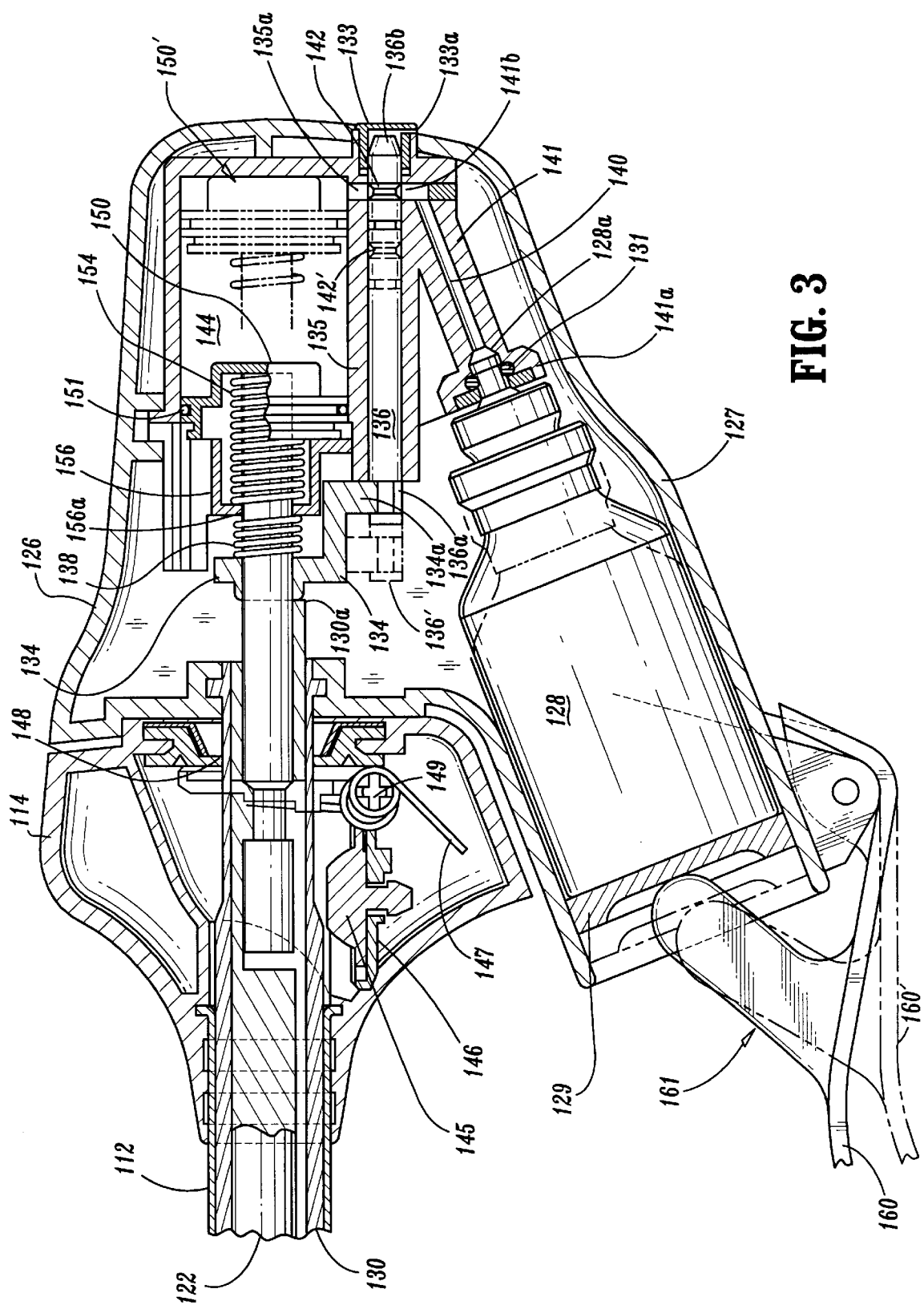
FIG. 3 is a cut-away partially sectional view of the proximal portion of the apparatus of the present invention.

Referring now to FIG. 3, the proximal end 130a of actuator 130 contacts movable flange 134, which is distally biased by means of helical compression spring 138. The bottom end of flange 134 includes a member 134a for engaging slot 136a of cylindrical shuttle valve 136. Shuttle valve 136 is slidably movable within valve housing 135. When the apparatus is in the inactivated condition the distal end of the shuttle valve is located in position 136' and aperture 142 of the shuttle valve is located in position 142'. Shuttle valve 136 includes an aperture 142 which is alignable with aperture 135a of the shuttle valve housing 135. Proximal end 136b of the shuttle valve is tapered.

A flapper 145, is mounted to flapper holder 146 which is pivotally mounted at hinge 149. Torsion spring 147 biases the flapper holder 146 to a position wherein flapper 145 obstructs aperture 148 in housing 114, thereby preventing the passage of gaseous or liquid fluids into or out of the body through the cannula 112 when the trocar portion 102 is withdrawn. Flapper 145 may be fabricated from a resilient material such as rubber or a rubber like polymer.

Proximal housing 126 includes a handle portion 127 in which a source of compressed gas, i.e., container 128, is stored, and a movable retainer plate 129 for retaining gas container 128 within handle 127. Trigger 160 is pivotally mounted at its proximal end to the handle 127 and includes an upright portion 161. Trigger 160 and upright portion 161 are configured and dimensioned such that when the trigger 160 is pressed or pivoted from unfired position 160' to fired position 160 the upright 161 presses into the retainer plate 129 thereby urging the gas container 128 proximally. The container 128 includes a metering nozzle 128a seated in corresponding nozzle reception port 141a in receiving member 141. O-ring 131 helps to provide a secure gas tight seal for preventing leakage of compressed gas. When the trigger 160 is released after firing, the removal of biasing force on the gas cylinder 128 releases pressure of nozzle 128a onto the O-ring 131 thereby permitting gas to discharge through the seal.

Metering nozzle 128a is biased towards a closed position extending outwardly from gas bottle 128. When pressed inward, metering nozzle 128a allows a predetermined amount of gas to be released from the bottle. Hence, pressing trigger 160 charges pressurized gas to the apparatus.

Receiving member 141 possesses a channel 140 for providing a flow path for the gas discharged from the bottle 128. Channel 140 extends to aperture 141b. When the shuttle valve 136 is in the proximal position (i.e., when the apparatus is activated) shuttle valve aperture 142 aligns with aperture 141*b* and aperture 135*a*, thereby opening a passage for gas to flow therethrough.

Piston 150 is slidably movable within chamber 144 between an unfired proximal position 150' and the distal or "fired" position 150, and is biased proximally by compression spring 154. O-ring 151 insures a gas tight seal. The distal end of spring 154 abuts stationary flange 156. Shaft 122 is slidably disposed through aperture 134*b* in the movable flange, and aperture 156*a* in the stationary flange. springs 138 and 154 are disposed around shaft 122. Shaft 122 is fixedly connected to piston 150 so that when the piston 150 is moved by entry of compressed gas into chamber 144, the obturator 122 is moved forward, i.e., distally, to expose cutting tip 124 from the cannula.

In operation the powered trocar is positioned by the surgeon such that actuator tube 130 is pressed against a wall of body tissue. The proximal end of actuator 130 moves proximally against the biasing force of spring 138, thereby pushing movable flange 134 which, in turn, moves shuttle valve 136 such that aperture 142 aligns with apertures 141*b* and 135*a*. By pressing trigger 160, nozzle 128*a* of gas cylinder 128 is pressed into receiving port 141*a* thereby releasing a metered amount of gas which is then introduced into piston chamber 144 via channel 140 and apertures 141*b*, 142 and 135*a*. The compressed gas then drives piston 150 distally thereby advancing cutting tip 124 to a position wherein the cutting tip protrudes beyond the distal end of cannula 112 so as to cut through the wall of body tissue. This is the position illustrated in FIGS. 1, 2*a* and 3. when the trigger 160 is released the gas seal between nozzle 128*a* and receiving port 141*a* is loosened thereby permitting the escape of compressed gas from the chamber 144. Thus, the biasing force of the spring 154 urges the piston 150 proximally and the cutting tip 124 is retracted. It should be noted that the tapered end portion 136*b* of the shuttle valve will also permit the gas from piston chamber 144 to escape. Thus, if for some reason the surgeon using the powered trocar apparatus 100 were to withdraw the apparatus from contact with body tissue while still pressing the trigger, or if the trocar tip penetrated into a body cavity, actuator 130 would return to its distal position under the biasing force of spring 138, as would shuttle valve 136. proximal end portion 136*b* of the shuttle valve would then align with aperture 135*a*, and gas within chamber 144 would then exit from chamber 144 through aperture 135*a* and a rear release aperture 133*a* in end cap 133. Thus, the trocar tip 124 cannot be exposed to body tissue unless actuator 130 is pressed inward to its activated proximal position.

The trigger 160 may be pressed as often as required to repeatedly advance the cutting tip 124. When a body cavity has been reached, the actuator 130 automatically slides forward due to the biasing force of spring 138. Shuttle valve 136 also slides forward thereby moving aperture 142 out of alignment with apertures 137 and 141*b*. The distal cutting tip 124 retracts and further firing of the instrument is impossible since the passageway for communicating gas to the piston chamber is closed. The actuator 130 thereby serves as sensor means for detecting whether the distal end of the instrument is in contact with body tissue, as well as a means for placing the instrument in an activated condition.

SECOND EMBODIMENT

FIGS. 4 to 9 illustrate a second embodiment 200 of the present invention.

As with the first embodiment 100, the second embodiment 200 must be put into an activated condition in order to permit firing of the trocar. Unlike the first embodiment 100, the actuator of the second embodiment 200 is not directly pressed against body tissue and does not serve as a means to detect whether the trocar tip has penetrated a wall of body tissue and entered a cavity. Rather, the trocar cutting tip itself is included in the body tissue sensing means: if it initially meets no resistance the instrument will not fire.

The overall shape and external appearance of the second embodiment 200 is similar to that of the first embodiment 100 as shown in FIG. 1, with the exception that there is no actuator projecting distally from the cannula, such as actuator 130 in FIG. 1.

Figure 4:
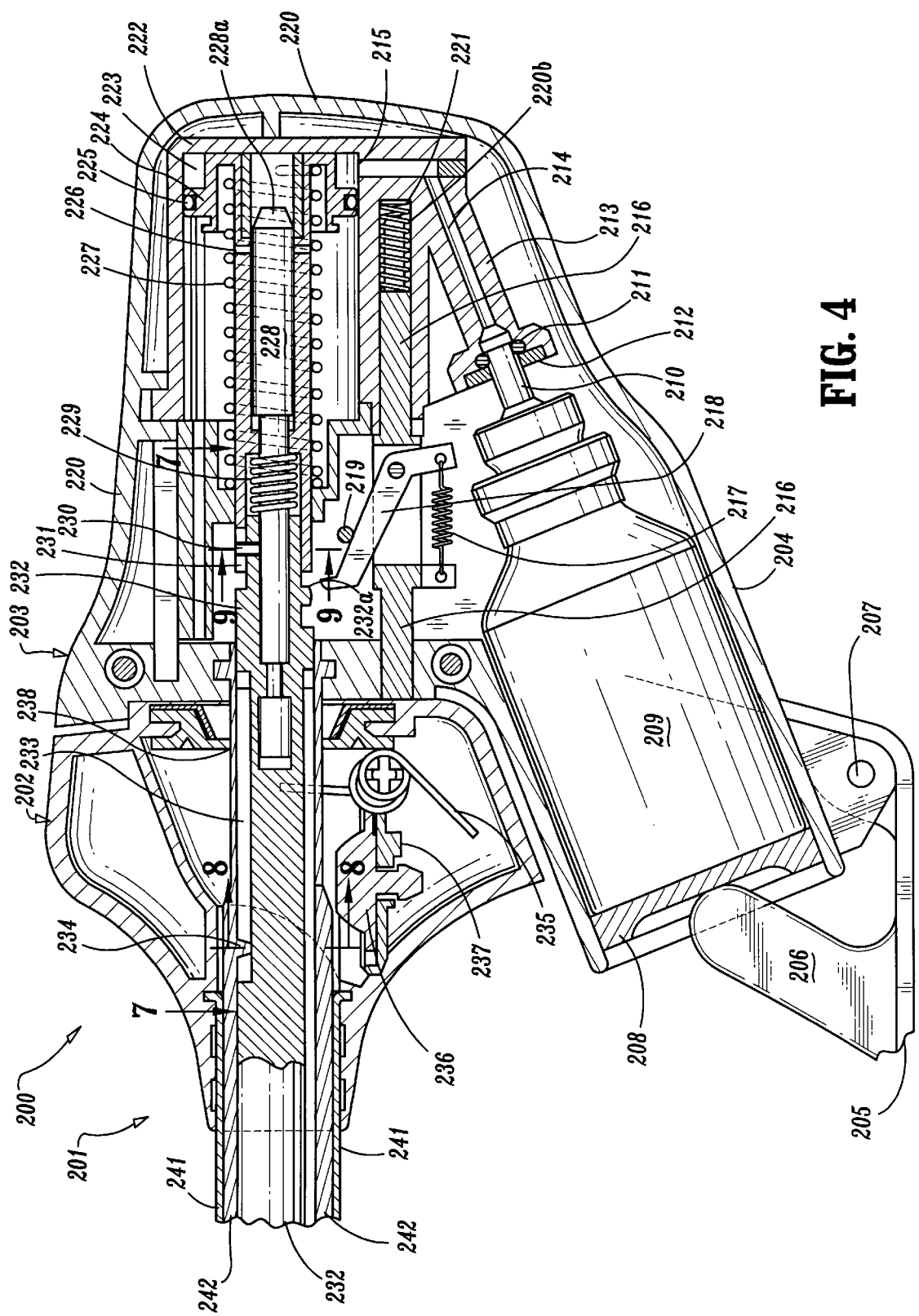
FIG. 4 is a cut-away partially sectional view of the proximal portion of a second embodiment of the apparatus of the present invention in prefired condition.

Referring now to FIG. 4, which shows the instrument 200 in an activated pre-fired condition, powered trocar assembly 200 generally comprises a distal endoscopic portion 201 which includes a cannula 241 and distal housing 202, and a powered trocar 203, which cooperatively engages the cannula portion to form the trocar assembly 200.

The powered trocar 203 includes housing 220 which contains and/or supports the various functioning parts of the powered trocar.

Activation of the powered trocar 203 is achieved by assembling the powered trocar 203 and endoscopic cannula portion 201 and pressing them together. FIG. 6 illustrates the configuration of the powered trocar 203 and cannula portion 201 assembled together but not yet pressed flush against each other. Actuator bottom 216 protrudes beyond the distal surface of the powered trocar. When the powered trocar 203 and the cannula portion 201 are pressed together the actuator button 216 is pushed distally to the inside of the housing 220 as shown in FIG. 4.

Actuator 216 is an elongated member slidably mounted within housing 220 and having a distal end 216*a* which is able to protrude through aperture 220*a* in the housing.

Figure 4A:
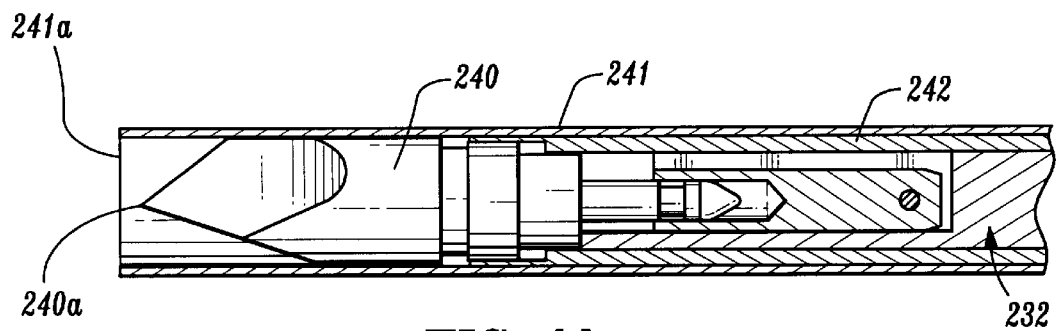
FIG. 4a is a cut-away partially sectional view of the distal end of the second embodiment in a prefired condition.
Figure 4B:
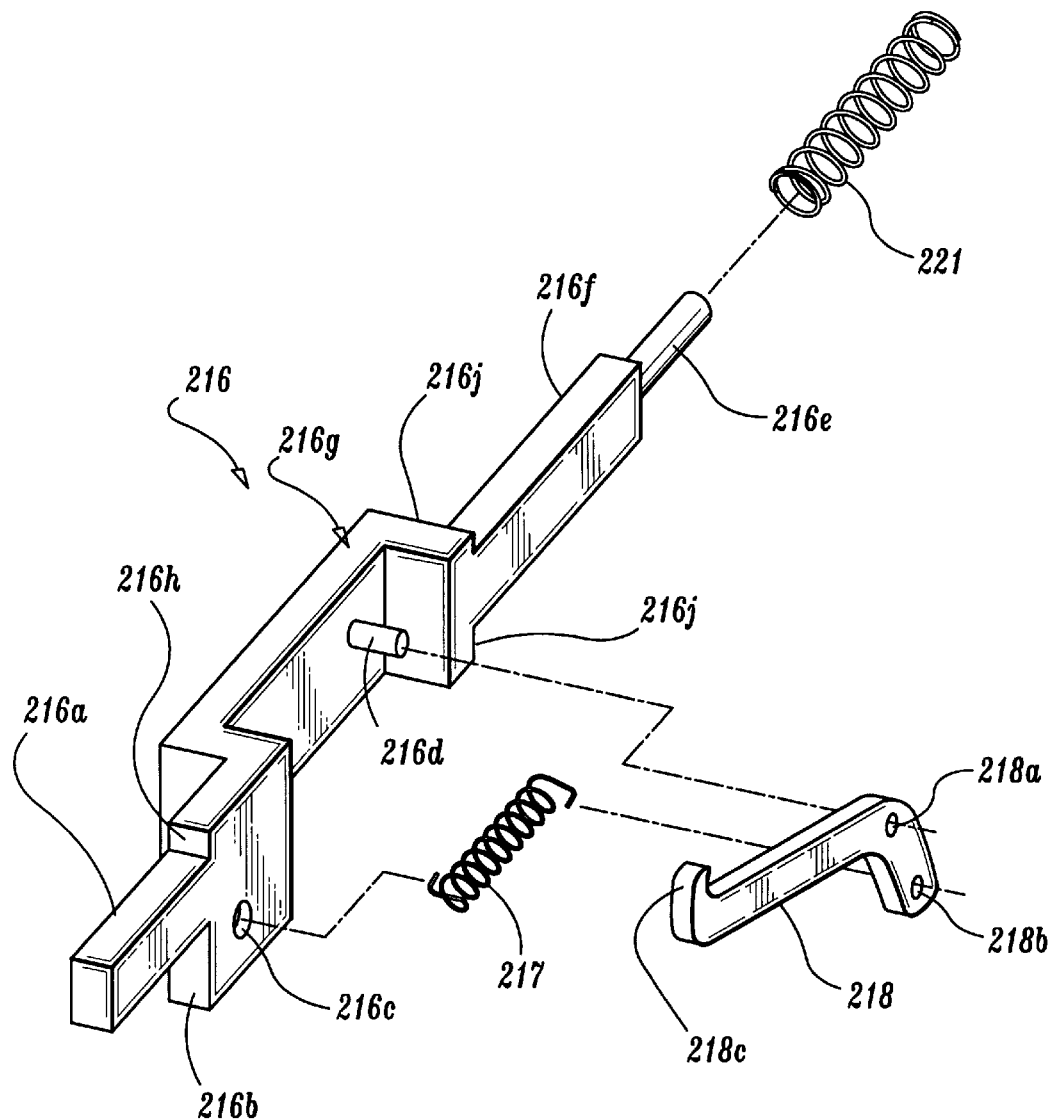
FIG. 4b is a perspective view of the actuation mechanism of the second embodiment.

Referring to FIG. 4*b*, actuator 216 has a depending portion 216*b* with aperture 216*c* for receiving the distal end of spring 217. A laterally projecting pin 216*d* provides a pivot point upon which latch 218 is mounted. At its proximal or rearward end, actuator 216 includes a proximal section 216*f* and pin 216*e* projecting proximally therefrom for mounting compression spring 221, which biases actuator 216 towards the distal position. Mid section 216*g* is offset to allow for the width of latch 218, and extends higher and lower than distal and proximal sections 216*a* and 216*f* in order to provide distal and proximal stopping surfaces 216*h* and 216*j*, respectively, to limit the longitudinal sliding motion of the actuator 216. The proximal portion 216*f* rides in chamber 220*b* (see FIG. 4 and 6) in the interior of housing 220.

Latch 218 includes aperture 218*a* for receiving pivot pin 216*d*, aperture 218*b* for receiving the proximal end of spring 217 and an upper hook portion 218*c* for catching and holding detent 232*a* of the obturator. Latch 218 is biased by expansion spring 217 towards a clockwise rotation around pivot 216*d*.

The Trigger Assembly

Figure 5A:
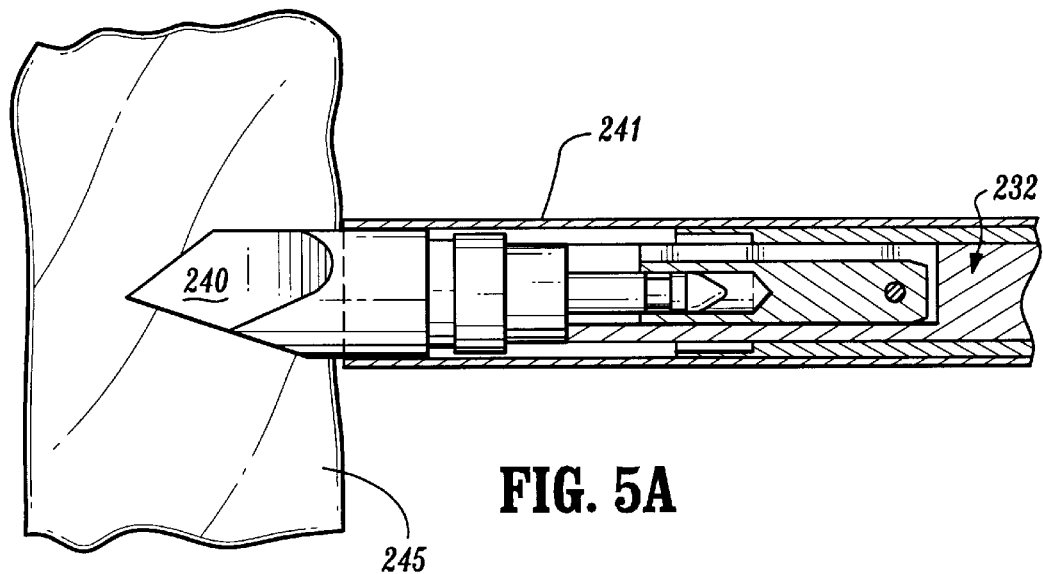
FIG. 5a is a partially sectional view of the distal end of the second embodiment in fired condition.
Figure 5:
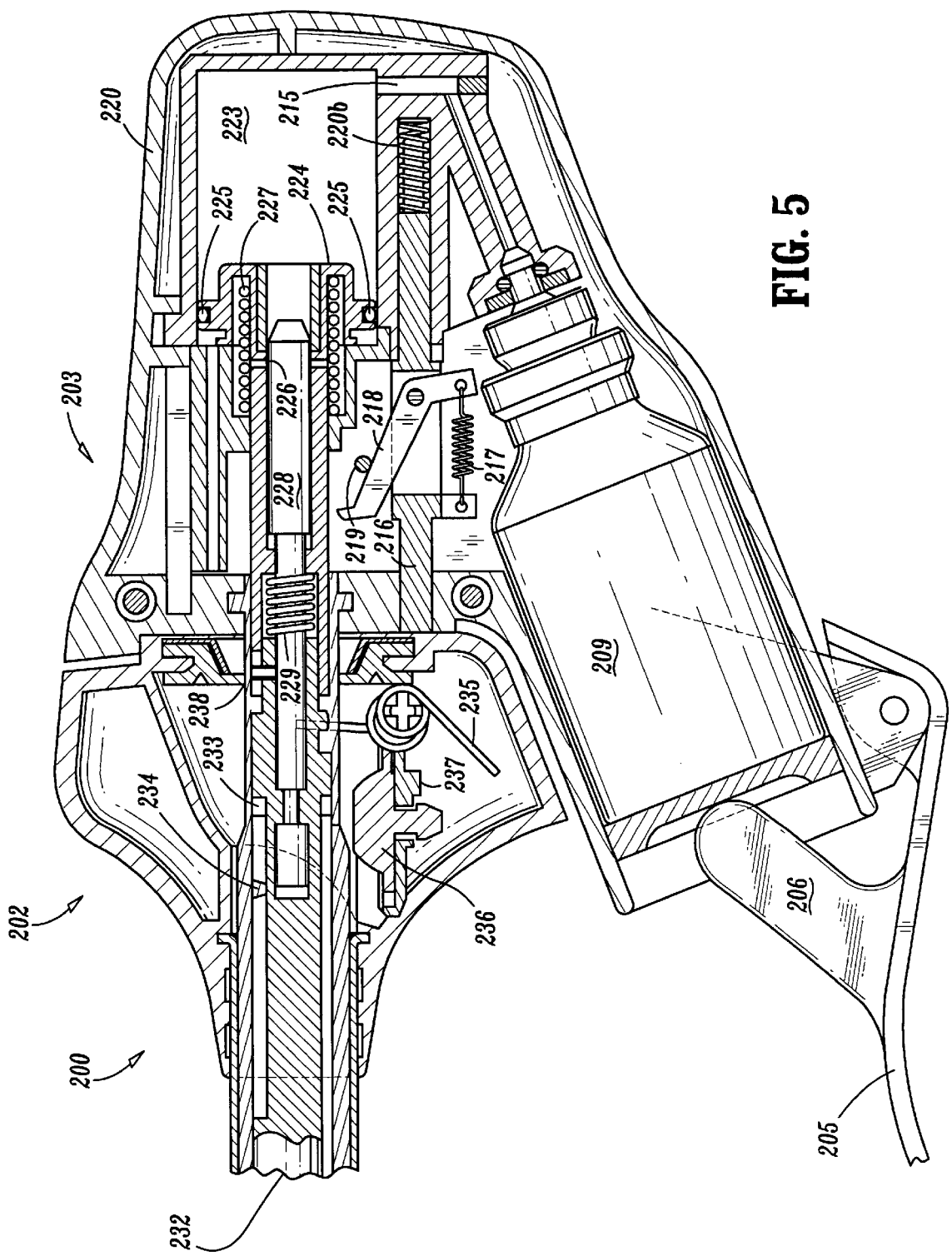
FIG. 5 is a cut-away partially sectional view of the proximal portion of the second embodiment in a fired condition.

Referring to FIGS. 4 and 5, housing 220 includes a handle portion 204 having means for receiving a source of pressurized gas, i.e., gas cylinder 209. Trigger 205 is pivotally mounted to the handle at pivot pin 207. Trigger 205 includes an upright member 206 for pressing into the distal portion of the handle 204. Gas cylinder 209 is slidably mounted in the handle 204 and is held therein by retainer 208, which is also movable. When trigger 205 is pressed, i.e., rotated clockwise, upright member 206 presses into retainer 208 and moves it proximally a short distance. Gas cylinder 209 is likewise moved proximally so that metering nozzle 210 of the gas cylinder presses into reception port 212 of the gas cylinder receiving arm 213. The O-ring 211 provides for a gas tight seal. When metering nozzle 210 is pressed into reception port 210 is releases a predetermined amount of pressurized gas which flows through channel 214 up to and through aperture 216 whereupon the pressurized gas enters chamber 223 and pushes piston 224 distally. O-ring 225 provides a gas tight seal between piston 224 and the chamber interior wall.

The Drive Assembly

The drive assembly of the present invention incorporates a piston which is distally movable against a biasing force in response to the application of a drive pressure, an obturator, and means for releasing the drive pressure in response to the absence of resistance (by body tissue) to distal movement encountered by the obturator. The movement of the obturator of the present embodiment may be described with respect to two frames of reference: one frame of reference is with respect to the piston and the other frame of reference is with respect to the apparatus as a whole. The obturator has a proximal position and a distal position with respect to the piston. In the distal position an escape vent is uncovered thereby releasing the driving pressure. In the proximal position, the escape vent is blocked thereby allowing the entire drive assembly to move distally. Means responsive to tissue resistance are provided to maintain the proximal position of the obturator in the first frame of reference as the obturator moves distally with respect to the apparatus as a whole.

Figure 4C:
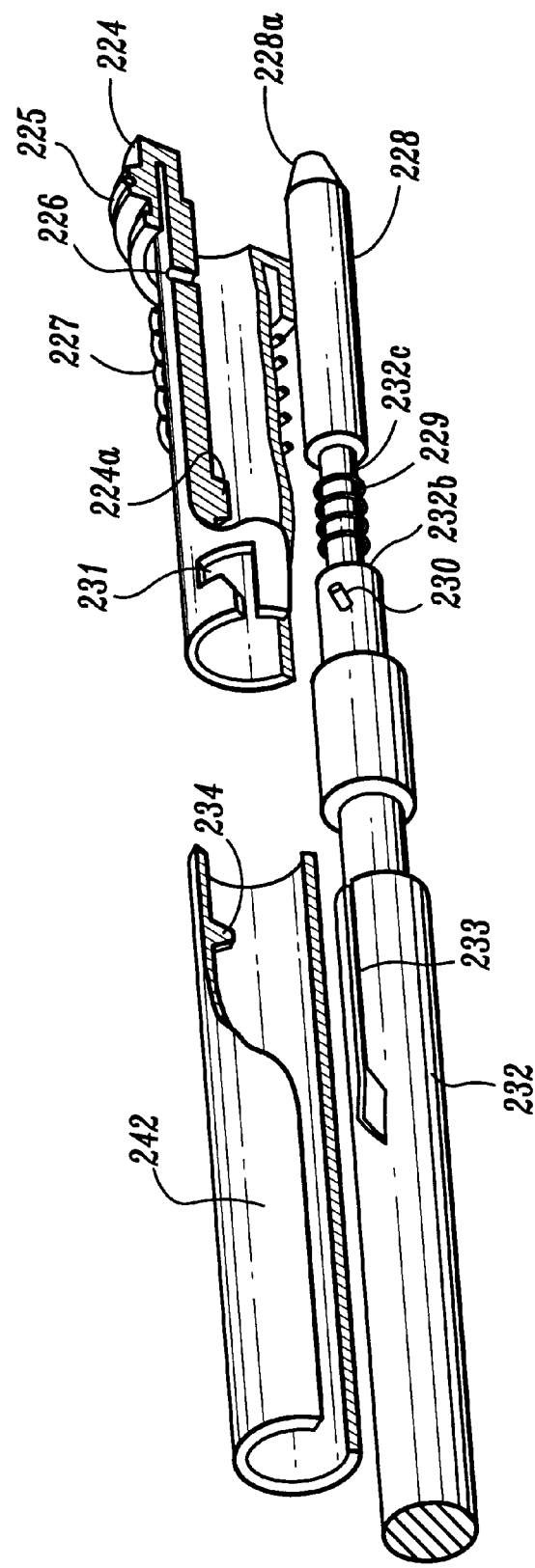
FIG. 4c is an exploded perspective view illustrating the drive mechanism of the second embodiment.

Referring now to FIG. 4c, obturator 232 is slidably mounted within a stationary (i.e., stationary with respect to the instrument housing) obturator housing 242, which has a depending boss 234. Depending boss 234 is adapted to fit into cam slot 233 in the obturator. The obturator is also axially slidable within the hollow bore of elongated piston 224. Piston 224 includes a vent 226, a locking slot 231 and an internally projecting backstop 224a. The obturator 232 includes an upright boss 230 which is engageable with locking slot 231. Rear shaft portion 228 of the obturator includes a tapered proximal end portion 228a. Obturator spring 229 is disposed around recessed portion 232c of the obturator 232. The proximal end of spring 229 abuts the distal surface of backstop 224a, and the distal end of spring 229 abuts surface 232b of the obturator 232 so as to exert a distally directed biasing force on the obturator. Piston spring 227 is disposed around the piston 224 and exerts a proximal directed biasing force on the piston.

Referring now to FIGS. 6, 7, 8, and 4c, the drive mechanism acts in the following manner. FIG. 7 illustrates the various configurations of bosses 234 and 230 at different stages in the instrument's operation. When the instrument is in the initial condition as illustrated in FIG. 6, the configuration of the bosses 234 and 230 is at positions 234a and 230a. When the cannula portion 201 and powered trocar 203 are pressed together (FIG. 4) the latch 218, by engaging holding detent 232a of the obturator, moves the obturator proximally against the biasing force of spring 229. Referring to FIG. 7, proximal movement of the obturator 232 forces it to rotate due to the camming action of depending boss 234 on the distal edge 233a of cam slot 233, thereby being placed in position 234b relative to slot 233. It should be noted with respect to FIG. 7, that the depending boss 234 is stationary, and it is the obturator which is moving. When the obturator 232 is rotated and moved proximally the upright boss 230 moves from position 230a to position 230b where it is engaged in slot 231.

When the apparatus is fired, compressed gas enters chamber 223 thereby forcing the piston to move distally against the biasing force of piston spring 227. Obturator 232 also moves distally, and with such distal movement the proximal camming edge 233b of the cam slot contacts depending boss at position 234c and the obturator 232 is rotated to its initial orientation. Upright 230 moves to position 230c whereupon it is no longer engaged in locking slot 231. At this position the obturator 232 sensitive to the resistance of body tissue. If no body tissue is present, i.e., if the trocar has already penetrated a wall of body tissue and has reached an internal body cavity, there will be no resistance and spring 229 will bias the obturator a short distance distally with respect to the piston. This movement aligns the tapered portion 228a of the proximal obturator shaft 228 with vent 226 thereby allowing the compressed gas to escape from chamber 223. Chamber 223 thus depressurizes and piston 224 is forced back to its proximal position. The obturator cannot be moved any farther in the distal direction. If, however, the trocar tip does encounter the resistance of body tissue, i.e., sufficient resistance to overcome the biasing force of spring 229, then the vent 226 will remain blocked by the proximal position of the obturator shaft 228 with respect to the piston 224, and the entire drive assembly will move distally. The depending boss 234 will ride through the extended proximal portion 233c of the slot to configuration 234d. O-ring 225 ensures a gas tight seal between the piston 224 and the inside walls of cylindrical chamber 223.

The size and strength of spring 229 will determine how sensitive the obturator is to tissue resistance. Thus, a relatively strong spring 229 will require strong tissue resistance from, for example, skin or muscle, in order to complete the firing sequence. Softer tissue such as internal organs, blood vessels and the like, or no tissue, will offer insufficient resistance and the firing sequence will not be completed. If a weaker spring 229 is employed then the powered trocar will complete the firing even if soft tissue is encountered. Thus, the size and strength of spring 229 may be chosen to suit the type of tissue to be operated on.

The Distal Cutting Feature

Figure 6A:
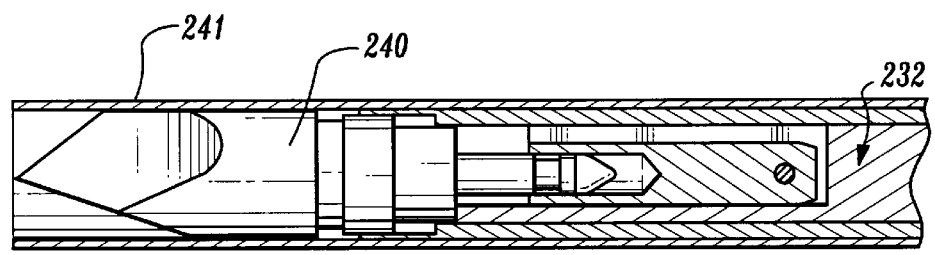
FIG. 6a is a partially sectional view of the distal portion of the second embodiment with the point of the distal cutting tip advanced to the distal opening of the cannula.

Referring to FIGS. 4a, 5a and 6a, the powered trocar includes a distal cutting tip 240 which is mounted to the distal end of obturator 232. In the initial position the trocar tip 240 is located within cannula 241 such that the distal point 240a of the cutting tip is proximal to the distal aperture 241a of the cannula. When fired, the trocar point 240a is advanced to the distal aperture 241a as shown in FIG. 6a or to a slight distance beyond. Referring additionally to FIG. 7, when the trocar tip 240 is in the configuration as shown in FIG. 6a, the obturator has advanced to the stage where the depending boss 234 is in position 234c and the upright boss is in position 230c. Since upright boss 230 is no longer engaged in slot 231 the trocar tip must encounter sufficient tissue resistance at this time or spring 229 will move the obturator 232 forward with respect to the piston 224 thereby aborting the firing sequence. If, as in FIG. 5a, the appropriate tissue 245 is encountered, the firing mechanism will complete the firing sequence and trocar tip 240 will penetrate the tissue 245.

Although the firing sequence is described in stages it should be remembered that the operation is smooth and continuous through the firing sequence.

Other Features

As with the previously described embodiment, the present embodiment 200 includes a flapper 236 mounted to a pivotable flapper holder 237 which is biased by torsion spring 235 to a closed position wherein it covers aperture 238 in the cannula portion. The flapper prevents the passage of gaseous or liquid fluids when the trocar is removed from the cannula.

THIRD EMBODIMENT

FIGS. 10 to 14 pertain to a third embodiment 300 of the present invention.

As with the previously described embodiments, the third embodiment must be put into activated condition to permit firing of the trocar. The actuator comprises a slidable member which extends a short distance distally beyond the distal end of the cannula. The overall shape and external appearance of the instrument is similar to that shown in FIG. 1 except for the configuration of the actuator.

Figure 10:
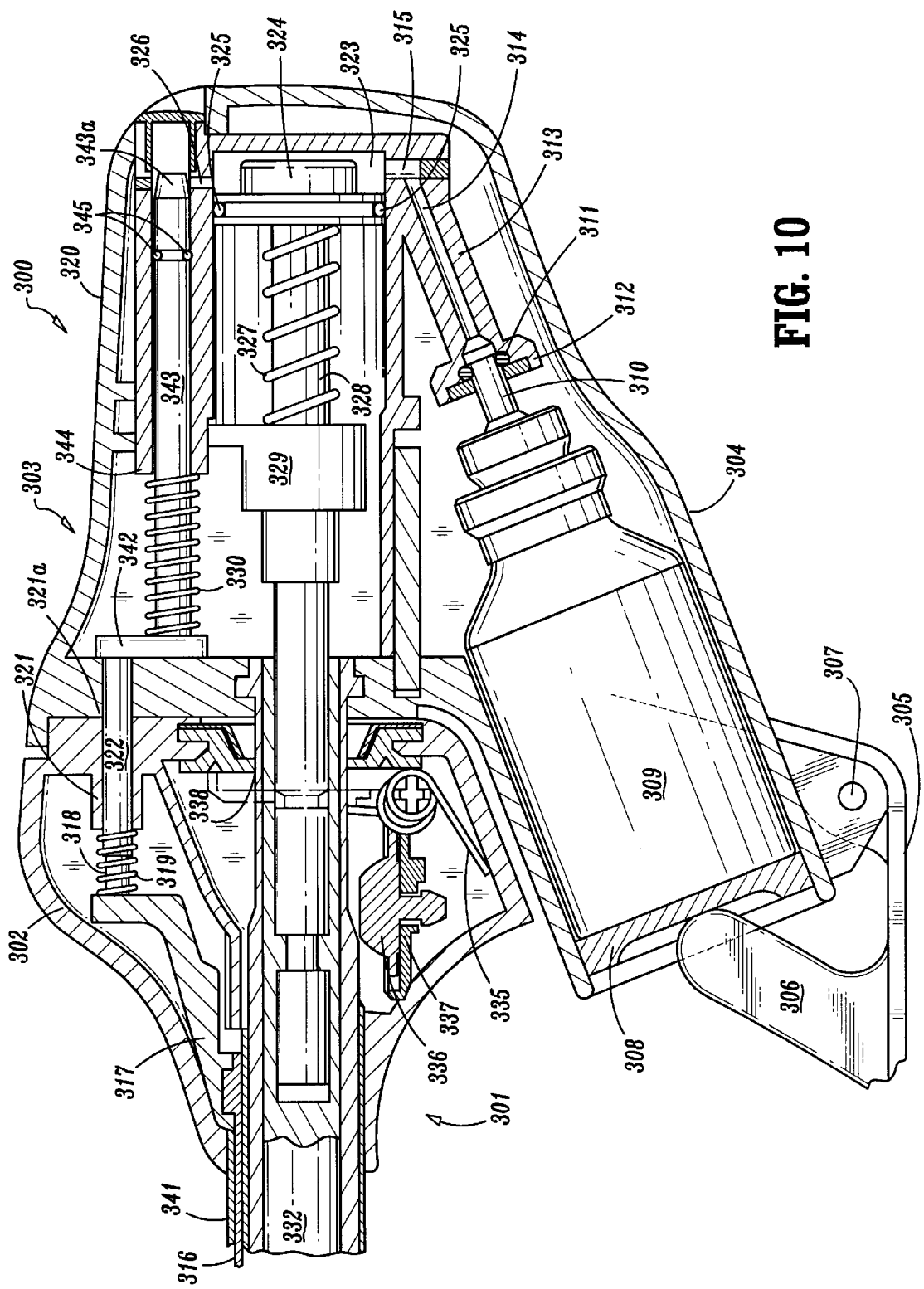
FIGS. 10 and 11 illustrate cut-away partially sectional views of a third embodiment of the apparatus of the present invention in prefired and fired conditions, respectively.

Referring now to FIG. 10 which shows the instrument in a pre-fired condition, powered trocar assembly 300 comprises a distal endoscopic portion 301 which includes a cannula 341 and distal housing 302, and a powered trocar 303 which cooperatively engages the distal portion 301 to form the trocar assembly 300.

The powered trocar 303 includes housing 320 which encloses and/or supports the various functioning parts of the powered trocar.

The Activation System

Activation of the powered trocar assembly 300 is achieved by the use of a sensor or actuator 316.

Figure 13:
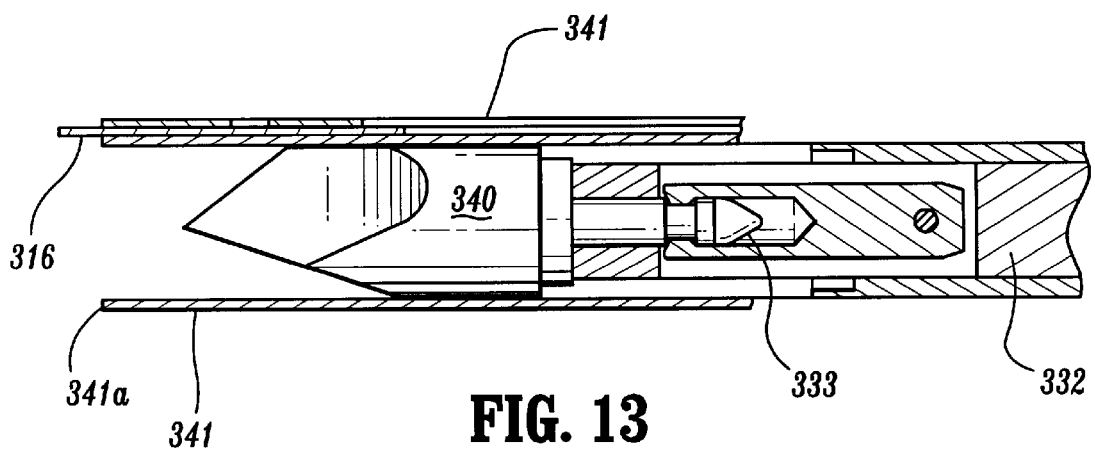

Referring to FIG. 13, which illustrates the distal end of the apparatus 300 in a pre-fired condition, cutting tip 340 of the trocar is mounted to the distal end of obturator 332 by means of a mounting fixture 333 and is located within cannula 341. Sensor 316 extends distally beyond the distal end 341a of the cannula 341.

Referring to FIG. 10, which shows the apparatus 300 in a pre-fired condition, the proximal end of sensor 316 is attached to sensor mounting fixture 317 which is slidably movable within the interior of housing 302. The sensor mounting fixture 317 has a proximally pointing cylindrical member 318, around which compression spring 319 is disposed. Spring 319 abuts guide member 321 and the proximal surface of sensor mounting member 317 so as to bias the sensor mounting member 317 to a distal position.

The powered trocar portion 302 includes a cylindrical member 322 which, when the apparatus is assembled, is slidably disposed through aperture 321a in the guide member 321. The distal end of member 322 abuts the proximal end of member 318 such that when member 318 is moved proximally, it pushed member 322 proximally.

Member 322 is fixedly attached to connector 342 which, in turn is attached to shaft 343. Helical compression spring 330 is disposed around the distal portion of shaft 343 and abuts connector 342 and the distal end of shaft housing 344 such that the connector 342, as well as member 322 and shaft 343 are biased to their distal position. Shaft 343 is axially slidable within housing 343 and possesses a tapered proximal end 343a. O-ring 345 provides a gas-tight seal for the shaft 343. Shaft 343 is slidable between a distal position wherein the tapered proximal end 343a is aligned so as to permit gas to flow through vent aperture 326 and the apparatus is in the inactivated and unfireable condition, and a proximal position wherein shaft 343 covers aperture 326 so that pressurized gas within chamber 323 cannot vent. When the distal end of cannula 341 is pressed against body tissue, the actuator 316 is moved proximally against the biasing force of spring 319, and, in turn moves member 321 proximally as well as connector 342 and shaft 343. This movement puts the apparatus 300 into an activated or ready to fire condition.

The Trigger Assembly

Figure 11:
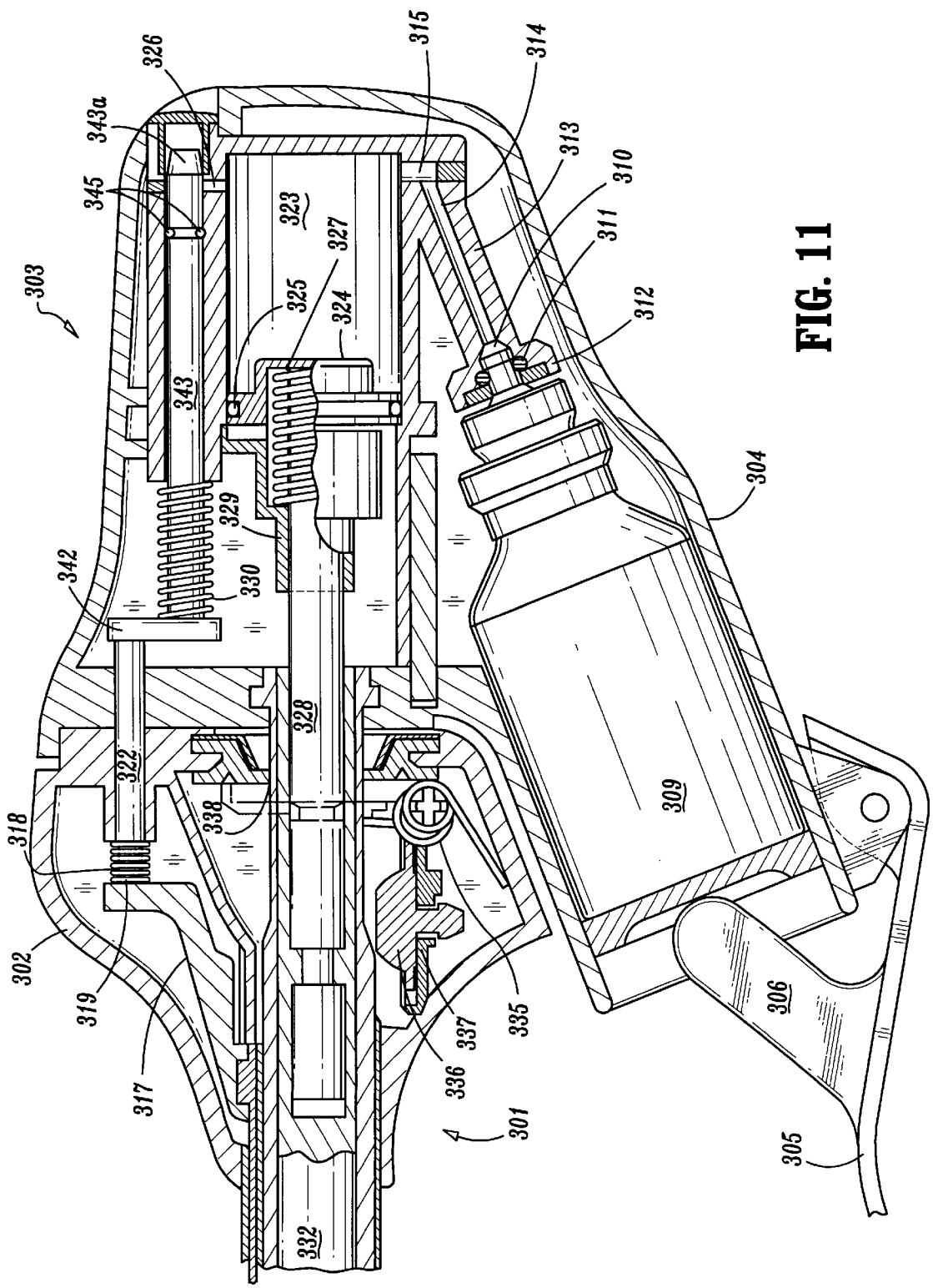

Referring to FIGS. 10 and 11, housing 320 includes a handle portion 304 having means for receiving a source of pressurized bas, i.e., gas cylinder 309. Trigger 305 is pivotally mounted to the handle at pivot pin 307. Trigger 305 includes an upright member 306 for pressing into the distal portion of the handle 304. Gas cylinder is slidably mounted in the handle 304 and is held therein by retainer 308, which is also movable. When trigger 305 is pressed, i.e., rotated clockwise, upright member 306 presses into retainer 308 and moves it proximally a short distance. Gas cylinder 309 is likewise moved proximally so that metering nozzle 310 of the gas cylinder presses into reception port 312 of the gas cylinder receiving arm 313. The O-ring 311 provides for a gas-tight seal. When metering nozzle 310 is pressed into reception portion 310 it releases a predetermined amount of pressurized gas which flows through channel 314 up to and through aperture 316 whereupon the pressurized gas enters chamber 323 and pushes piston 324 distally. O-ring 325 provides a gas-tight seal between piston 324 and the chamber interior wall.

The Drive Assembly

Referring to FIGS. 10 and 11, the apparatus 300 includes a piston 324 slidably positioned in chamber 323. O-ring 325 provides a gas-tight seal between the piston 324 and the interior wall of chamber 323. Obturator 332 includes a proximal shaft portion 328 which is attached to piston 324. Shaft 328 is slidable within an aperture in shaft mounting fixture 329. Helical compression spring 327 abuts the shaft mounting fixture 329 and piston 324 so as to bias the piston proximally.

When the trigger 305 is pressed, compressed gas enters chamber 323. If the apparatus is in the inactivated condition, the gas will vent through aperture 326 without causing the instrument to fire. If, however, the apparatus is in the activated condition, vent aperture 326 will be closed by shaft 343 and chamber 323 will pressurize thereby driving piston 324 distally against the biasing force of spring 327.

Figure 12:
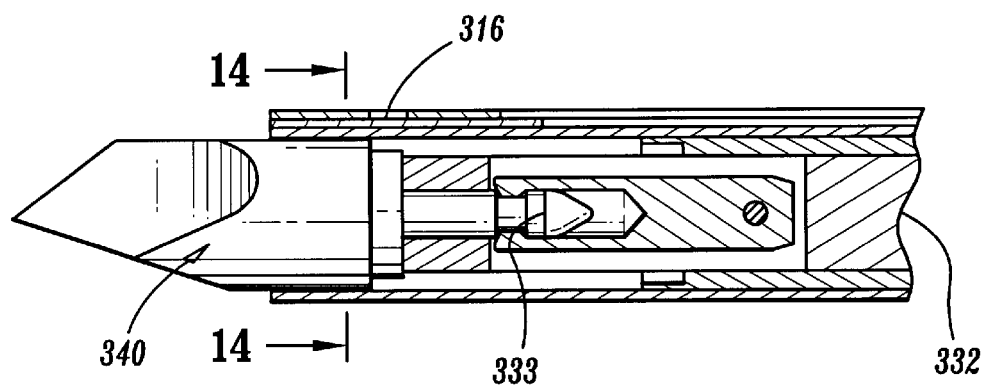
FIGS. 12 and 13 illustrate partially sectional views of the distal end of a third embodiment in fired and unfired conditions respectively.
Figure 14:
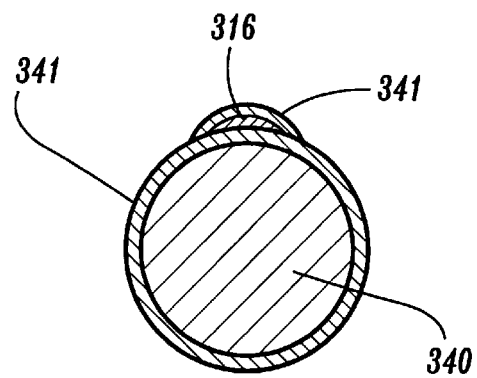
FIG. 14 illustrates an end sectional view of the distal end of the third embodiment.

Shaft 328 and the obturator 332 will accordingly be driven distally. Referring to FIG. 12, the distal cutting tip 340 will be advanced distally beyond the distal end of the cannula 341 so as to cut through body tissue.

Other Features

As with the previously described embodiments, the present embodiment 300 includes a flapper 336 mounted to a pivotable flapper holder 337 which is biased by torsion spring 335 to a closed position wherein it covers aperture 338 in the cannula portion. The flapper prevents the passage of gaseous or liquid fluids when the trocar is removed from the cannula.

FOURTH EMBODIMENT

Figure 15:
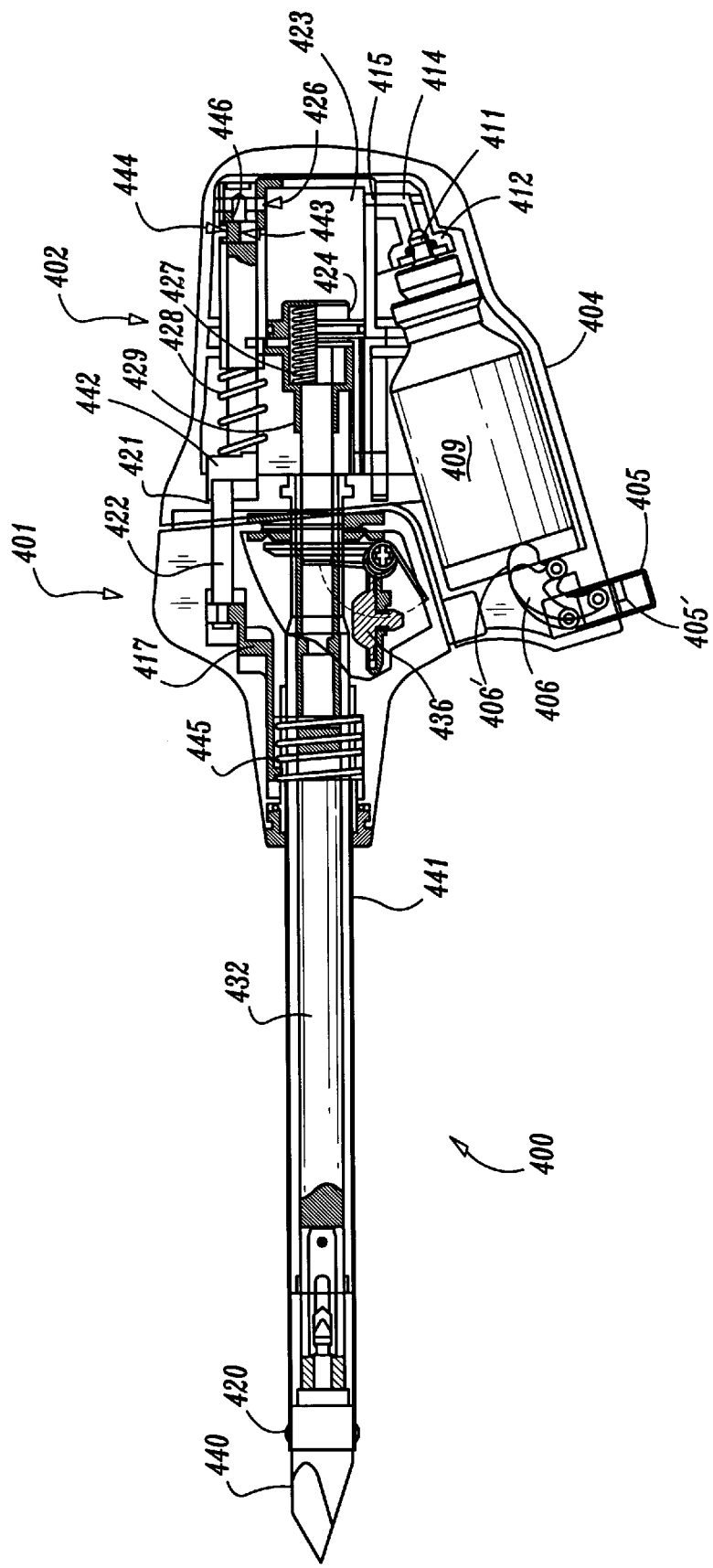
FIG. 15 illustrates a cut-away partially sectional view of a fourth embodiment of the present invention.

FIG. 15 illustrates a fourth embodiment 400 of the present powered trocar assembly invention in a fired condition. As with the previously describe embodiments, the endoscopic cannula portion 401 and the powered trocar portion 402 are assembled with obturator 432 inserted into cannula 441. The cannula 441 of this embodiment is biased to the distal position by spring 445. Sensor fixture 417 is connected to the proximal portion of the cannula 441 and is slidably mounted within the endoscopic cannula portion 401. Rod 422 is connected to sensor fixture 417 and extends proximally through aperture 421 in the powered trocar housing wherein rod 422 abuts shuttle valve 442. A resilient seal 443 is located at the proximal end of the shuttle valve. The resilient seal 443 comprises a plug of resilient material such as natural or synthetic rubber or a similar material.

Trigger 405 is button shaped and slidably mounted to the end of handle 404 of the instrument 400. When pressed, trigger 405 moves to position 405' and upright 406 is moved to position 406'. Nozzle 411 of gas cylinder 409 is thereby urged into docking port 412 and a metered amount of pressurized gas flows through bore 414 and through aperture 415 into chamber 423. If the instrument 400 is in the activated condition, chamber 423 pressurizes and piston 424 is moved distally against the biasing force of piston spring 427. The proximal end portion of obturator 432 is slidably disposed through fixture 429 and is attached to piston 424. A cutting tip 440 is located at the distal end of the obturator. When piston 424 is moved, obturator 432 likewise moves distally, and cutting tip 440 is advanced to a position beyond the distal end of cannula 441 to perform the cutting operation. However, if the apparatus is not in an activated condition, pressurized gas entering chamber 423 exists via escape vents 426, 446, and 444 without advancing the piston 424.

The apparatus 400 is activated when the distal end of the cannula 441 is pressed against body tissue with sufficient counterforce to overcome the biasing force of spring 445. The cannula 441 is optionally provided with abutment means to facilitate interaction between the body tissue and the cannula 441. The abutment means can comprise, for example, a raised ridge 420 extending circumferentially around the distal end portion of the cannula to increase frictional interference with body tissue. The cannula then slides proximally relative to the rest of the instrument, and thereby moves fixture 417, rod 422, and shuttle valve 442 proximally against the biasing force of spring 428 such that shuttle valve 442 blocks exit aperture 444 and the resilient plug 443 abuts and seals escape vent 446. Chamber 423 is then permitted to pressurize when the trigger 405 is pressed.

As with the other previously described embodiments, when there is no body tissue to provide counterforce to the cannula (e.g., a body cavity is reached) the instrument 400 deactivates: cannula 441 springs forward thereby permitting shuttle valve 442 to move distally and open vents 444 and 446. When the cutting operation is completed, the powered trocar portion 402 may be removed from the cannula portion 401 whereupon flapper valve 436 closes to prevent the entry to or egress from the body of gas or other fluids via cannula 441.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A trocar for placement in the lumen of a cannula to facilitate inserting the cannula through the wall of a body cavity, the trocar comprising a handle, an obturator with a point for piercing the wall of the body cavity, and a protective sleeve mounted concentrically around the obturator, the obturator retracting proximally relative to the handle generally simultaneously as the protective sleeve advances distally relative to the handle after the trocar point has penetrated through the wall of the body cavity.

2. The trocar according to claim 1 wherein the protective sleeve advances distally with respect to the obturator after the trocar point penetrates through the wall of the body cavity, and wherein the obturator retracts proximally upon the distal advancement of the protective sleeve.

3. A trocar for placement in the lumen of a cannula to facilitate inserting the cannula through the wall of a body cavity, the trocar having a housing, an obturator with a point for piercing the wall of the body cavity, and a protective sleeve mounted concentrically around the obturator, and means for retracting the obturator proximally relative to the housing at approximately the same time the protective sleeve advances distally relative to the housing after the trocar point has penetrated through the wall of the body cavity.

4. The trocar according to claim 3 wherein the retracting means retracts the obturator after the cannula has penetrated through the wall of the body cavity.

5. The trocar according to claim 4 wherein the trocar comprises means for advancing the protective sleeve distally relative to the obturator after the trocar point has penetrated through the wall of the body cavity, and means for triggering the retracting means upon the relative distal advancement of the protective sleeve.

6. The trocar according to claim 5 wherein the protective sleeve can move axially with respect to the obturator, and is resiliently biased distally so that the protective sleeve can retract proximally relative to the obturator in response to drag from the wall of the body cavity as the trocar is advanced through the wall of the body cavity, and can advance distally after the cannula has penetrated through the wall of the body cavity and reduced the drag on the sleeve, and further comprising means for triggering the retracting means upon the distal advancement of the protective sleeve.

7. The trocar according to claim 4 wherein the protective sleeve can move axially with respect to the obturator, and is resiliently biased distally so that the protective sleeve can retract proximally relative to the obturator in response to drag from the wall of the body cavity as the trocar is advanced through the wall of the body cavity, and can advance distally after the cannula has penetrated through the wall of the body cavity and reduced the drag on the sleeve, and further comprising means for triggering the retracting means after the proximal retraction of the protective sleeve that occurs while the trocar is penetrating the wall of the body cavity, and the subsequent distal advancement of the protective sleeve that occurs after the cannula has penetrated through the wall of the body cavity.

8. The trocar according to claim 4 further comprising means for providing a tactile signal to the user when the obturator retracts, to signal the user that the trocar point has penetrated through the wall of the body cavity.

9. A trocar for placement in the lumen of a cannula to facilitate inserting the cannula through the wall of a body cavity, the trocar comprising:
   a handle;
   an obturator extending distally from the handle and having a point on its distal end for piercing the wall of the body cavity;
   a protective sleeve mounted concentrically around the obturator for axial movement relative to the obturator, and resiliently biased distally so that the protective sleeve can retract proximally relative to the obturator in response to drag from the wall of the body cavity as the trocar point is advancing through the wall of the body cavity, and can advance distally after the cannula has penetrated through the wall of the body cavity and reduced the drag on the protective sleeve; and
   means for retracting the obturator relative to the handle generally at the same time the protective sleeve advances distally relative to the handle after the trocar point has penetrated through the wall of the body cavity.

10. The trocar according to claim 9 further comprising means, responsive to the distal advancement of the protective sleeve for triggering the retracting means.

11. The trocar according to claim 10 further comprising means for preventing the triggering means from triggering the retracting means until after the protective sleeve has retracted proximally relative to the obturator, such as is caused by advancing the trocar through the wall of the body cavity, wherein the triggering occurs after the protective sleeve first moves proximally relative to the handle and then moves distally relative to the handle.

12. A trocar for placement in the lumen of a cannula to facilitate inserting the cannula through the wall of a body cavity, the trocar comprising:

a handle;

an obturator extending distally from the handle and having a point on its distal end for piercing the wall of the body cavity;

a protective sleeve mounted concentrically around the obturator for axial movement relative to the obturator, and resiliently biased distally so that the protective sleeve can retract proximally relative to the obturator in response to drag from the wall of the body cavity as the trocar point is advancing through the wall of the body cavity, and can advance distally after the cannula has penetrated through the wall of the body cavity and reduced the drag on the protective sleeve;

biasing means for biasing the obturator proximally relative to the protective sleeve;

means for releasably securing the obturator from proximal retraction under the bias of the biasing means; and means for releasing the releasable securing means upon the proximal retraction of the protective sleeve that occurs while the trocar is advancing through the wall of the body cavity, and the subsequent distal advancement of the protective sleeve that occurs after the cannula has penetrated through the wall of the body cavity.

13. A trocar for placement in the lumen of a cannula to facilitate inserting the cannula through the wall of a body cavity, the trocar comprising a housing, an obturator with a point for piercing the wall of the body cavity, and a member mounted adjacent the obturator, the obturator retracting proximally relative to the housing in response to the member advancing distally relative to the housing.

14. A trocar for placement in the lumen of a cannula to facilitate inserting the cannula through the wall of a body cavity, the trocar comprising a housing, an obturator with a point for piercing the wall of the body cavity, and a tubular member mounted concentrically around the obturator, the tubular member defining a distal portion which is adapted to extend beyond the cannula, the obturator retracting proximally relative to the housing generally simultaneously as the tubular member advances distally relative to the housing.

15. The trocar according to claim 14, wherein the distal portion is at least partially tubular.

16. A trocar for placement in the lumen of a cannula to facilitate inserting the cannula through the wall of a body cavity, the trocar having a housing, an obturator with a point for piercing the wall of the body cavity, and a member mounted adjacent the obturator, and means for retracting the obturator proximally relative to the housing at approximately the same time the member advances distally relative to the housing.

17. A trocar for placement in the lumen of a cannula to facilitate inserting the cannula through the wall of a body cavity, the trocar having a housing, an obturator with a point for piercing the wall of the body cavity, and a member mounted adjacent the obturator, and means for retracting the obturator proximally relative to the housing at approximately the same time the member advances distally relative to the housing after the trocar point has penetrated through the wall of the body cavity.

18. A trocar for placement in the lumen of a cannula to facilitate inserting the cannula through the wall of a body cavity, the trocar having a housing, an obturator with a point for piercing the wall of the body cavity, and a tubular member mounted concentrically around the obturator, the tubular member defining a distal portion which is adapted to extend beyond the cannula, and means for retracting the obturator proximally relative to the housing at approximately the same time the tubular member advances distally relative to the housing after the trocar point has penetrated through the wall of the body cavity.

19. A trocar according to claim 18, wherein the distal portion is at least partially tubular.

20. A trocar for placement in the lumen of a cannula to facilitate inserting the cannula through the wall of a body cavity, the trocar comprising:

a handle;

an obturator extending distally from the handle and having a point on its distal end for piercing the wall of the body cavity;

a member mounted adjacent the obturator for axial movement relative to the obturator, the member being resiliently biased distally;

wherein the member is adapted to retract proximally relative to the obturator in response to drag from the wall of the body cavity and to advance distally after the cannula has penetrated through the wall of the body cavity, and wherein the obturator is adapted to move proximally in response to distal movement of the member.

21. A trocar for placement in the lumen of a cannula to facilitate inserting the cannula through the wall of a body cavity, the trocar comprising:

a handle;

an obturator extending distally from the handle and having a point on its distal end for piercing the wall of the body cavity;

a tubular member mounted concentrically around the obturator for axial movement relative to the obturator, the tubular member being resiliently biased distally;

wherein the tubular member is adapted to retract proximally relative to the obturator in response to drag from the wall of the body cavity and to advance distally after the cannula has penetrated through the wall of the body cavity, and wherein the obturator is adapted to move proximally in response to distal movement of the tubular member.

* * * * *